(12) United States Patent
Chen et al.

(10) Patent No.: US 6,942,777 B2
(45) Date of Patent: Sep. 13, 2005

(54) SAMPLE ANALYSIS SYSTEM WITH CHIP-BASED ELECTROPHORESIS DEVICE

(75) Inventors: Shu-Hui Chen, No. 1, Ta-Hsueh Road, Tainan (TW); Gwo-Bin Lee, Tainan (TW); Chung-Shi Yang, Nantou Shien (TW); Yi-Hung Lin, Tainan (TW); Wan-Chou Sung, Tainan (TW); Guan-Ruey Huang, Tainan (TW)

(73) Assignee: Shu-Hui Chen, Tainan (TW)

( * ) Notice: Subject to any disclaimer, the term of this patent is extended or adjusted under 35 U.S.C. 154(b) by 629 days.

(21) Appl. No.: 09/880,801

(22) Filed: Jun. 15, 2001

(65) Prior Publication Data

US 2002/0079224 A1 Jun. 27, 2002

(30) Foreign Application Priority Data

Dec. 13, 2000 (TW) .......................... 89126609 A

(51) Int. Cl.$^7$ .................. C25B 11/00; G01N 27/453
(52) U.S. Cl. ................ 204/604; 204/601; 204/600; 204/453; 204/451; 204/450
(58) Field of Search ................. 204/450, 451, 204/453, 600, 601, 604

(56) References Cited

U.S. PATENT DOCUMENTS 4,415,428 A * 11/1983 Nochumson et al. ........ 204/606
6,013,168 A * 1/2000 Arai ........................... 204/601

OTHER PUBLICATIONS

Chiem et al., Microchip–based capillary electrophoresis for immunoassays: analysis of monoclonal antibodies and theophylline Anal. Chem., 69, 373–378 (1997).*

Chiem et al., "Microchip systems for immunoassay: an integrated immunoreactor with electrophoretic separation for serum theophylline determination", Clinical Chemistry, 44(3), 591–598(1998).*

Seiler et al., "Planar glass chips for electrophoresis: repetitive sample injection, quantitation, and separation efficiency", Anal. Chem., 65, n1481–1488(1993).*

Seiler et al., Electroosmotic pumping and valveless control of fluid flow within a manifold of capillaries on a glass chip, Anal. Chem., 66, 3485–3491(1994).*

Jacobson et al., "Fused quartz substrates for microchip electrophoresis", Anal. Chem., 67, 2059–2063(1995).*

* cited by examiner

*Primary Examiner*—Ling-Sui Choi
(74) *Attorney, Agent, or Firm*—Bacon & Thomas, PLLC

(57) ABSTRACT

The present invention relates to a sample analysis system with chip-based electrophoresis device, particularly, the chip electrophoresis is connected to the dynamic flow-based auto-sampling device to introduce the sample into the chip-based electrophoresis device. By utilizing the derivatization biochemistry method to have a surface modification on the sample loading channel, it prevents the sample from being adhered to the wall of the sample loading channel, and hence increases the sample loading rate, reduces cross-contamination of samples and performs specific bio-reaction by using the immobilization of matter including antigen, antibody, protein, or enzyme. This invention makes use of the continuous split flow and electric voltage control to work with the detecting unit, signal collecting unit, and signal processing unit so that the sample undergoes a timely, fast, continuous analysis without having interference from the sample of other time.

10 Claims, 19 Drawing Sheets

| Flow rate (μL/min) | Critical Pinching Voltage (KV) |
|---|---|
| 10 | 1.95 |
| 7 | 1.75 |
| 5 | 1.15 |
| 4 | 0.87 |
| 3 | 0.76 |
| 2 | 0.50 |
| 1 | 0.35 |

Fig. 8

SAMPLE ANALYSIS SYSTEM WITH CHIP-BASED ELECTROPHORESIS DEVICE

BACKGROUND OF THE INVENTION

1. Field of the Invention

The present invention relates to a sample analysis system with chip-based electrophoresis device, particularly, said chip electrophoresis is connected to a flow-based auto-sampling device by dynamic force for guiding the sample into the chip-based electrophoresis device. By utilizing the derivatization method of having a surface modification on the sample loading channel, it prevents the sample from being adhered to the channel wall of the sample loading channel, and hence increases the feeding rate, reduces cross contamination of samples and performs specific bio-reaction by using the immobilization of matter including antigen, antibody, protein, or enzyme. This invention makes use of the continuous split flow and electric voltage control to work with the detecting unit, signal collecting unit, and signal processing unit so that the sample undergoes a timely, fast, continuous analysis without having interference from the sample of other time.

2. Description of the Related Art

Ever since the development of capillary electrophoresis (CE), the advantages of its fast separation time, tiny injected volume of the sample, high sensitivity, and convenient instrument operation make it very popular in different applications in the analysis area [R. Kuhn, S, Hof. Kuhn, *Capillary Electrophoresis: Principles and Practice*, 1993, Springer-Verlag, Berlin Heidellergg N.Y. (U.S.A.)], Recently, the biotechnology develops rapidly, the analysis developed from the capillary electrophoresis is widely used in the deoxyribonucleic acid (DNA) analysis as the basic research [Roche, M. E.; Oda, R. P.; Landers, J. P. *BIOTECHNOLOGY PROGRESS*, 1997, 13, 659–668]. As the biotech and the semiconductor process technology progress, Manz in 1992 miniaturized the electrophoresis onto the microchip to perform the experiment of sample separation [Manz, A.; Harrison, D. J.; Verpoorte, E. M. J.; Fettinger, J. C.; Ludi, H.; Widmer, H. M. J. Chromatorgr. 1992, 593–258], and hence promoted the traditional capillary electrophoresis technology to a higher level of high-tech area—Chip Electrophoresis.

Since the semiconductor process technology is matured, the chip design has a wide range of variability, and all kinds of chips are designed according to different needs. This type of chip process technology has been reported. The chip electrophoresis is a high efficient analysis method for species of tiny quantity [K. Seiler, D. Jed Harrison. A. Manz. Analytical Chemistry 65(1993), 1481]. For example, [N. -H. Cheiem, D. J. Harrison. Electrophoresis19 (1998), 3040]; [N. -H. Cheiem, D. J. Harrison. Clinical Chemistry 44(3) 591] reported that the purified sample such as the deoxyribonucleic acid (DNA) product, enzyme, substrate, antibody, and antigen is placed in the sample trough of the chip for analysis.

However, the foregoing chip electrophoresis design is not able to perform continuous sampling for the analysis of the sample, and in view of the traditional capillary electrophoresis needs a complicated interface design for the continuous sample analysis. Such complicated interface will create lots of variability to the experiment including: (1) the distance between the fluid outlet and the capillary inlet; (2) the control of gate valve flow rate; (3) stop the gate valve flow rate and start the delay tune for the dialyzed sample, etc., and give rise to a variation in the experiment result. Therefore, the present invention provides a chip-based electrophoresis device and its analysis system to improve the shortcomings of the prior art technology, and further establishes a fast and timely analysis system for the continuous sampling.

SUMMARY OF THE INVENTION

In view of the shortcomings and disadvantages of the sample analysis operation and usage of the prior art technology, the present invention provides a sample analysis system with chip-based electrophoresis device, comprising a chip electrophoresis device, an auto-sampling device, a detecting unit, a signal collecting unit, and a signal processing unit; wherein the flow auto-sampling device comprises the following two modes for sampling procedure: Continuous mode of sample introduction, and discrete mode of sample introduction. The continuous mode such as sampling by microdialysis performs a continuous and instant sampling for animal samples. The discrete mode such as using the injector of different volume to introduce the sample into the chip. In addition, said chip can proceed with the surface modification on the sampling channel to prevent the sample being adhered onto the wall of the sampling channel, and further increase the sample loading rate and reduce cross contamination of samples. The present invention is a sample analysis system with chip-based electrophoresis device, which has a continuous sampling analysis function, and it connects the said chip electrophoresis device to the above automatic flow-based auto-sampling device by dynamic force. It also makes use of the continuous split fluid of the chip and the electric voltage control method to control and introduce the sample into said electrophoresis device, and works with said detecting unit to generate the signal of the sample, and then converts the signal via said signal collecting unit from analog to digital, followed by outputting the data via said signal processing unit. The data is for sample analysis, and the analyzed data is provided to the search unit and medical unit for the following related work of the research.

BRIEF DESCRIPTION OF THE DRAWINGS

Other objects, features, and advantages of the invention will become apparent from the following detailed description of the preferred but non-limiting embodiment. The description is made with reference to the accompanying drawings, in which:

FIG. 8 illustrates the relation between the flow rate and the critical pinching voltage of the sample analysis system with chip-based electrophoresis device of this invention.

DETAILED DESCRIPTION OF THE PREFERRED EMBODIMENTS

This invention relates to a sample analysis system with chip-based electrophoresis device 100. To make it easier for our examiner to understand the objective of the invention, its structure, innovative features, and its performance, we use a preferred embodiment together with the attached drawings for the detailed description of the invention.

Figure 1:
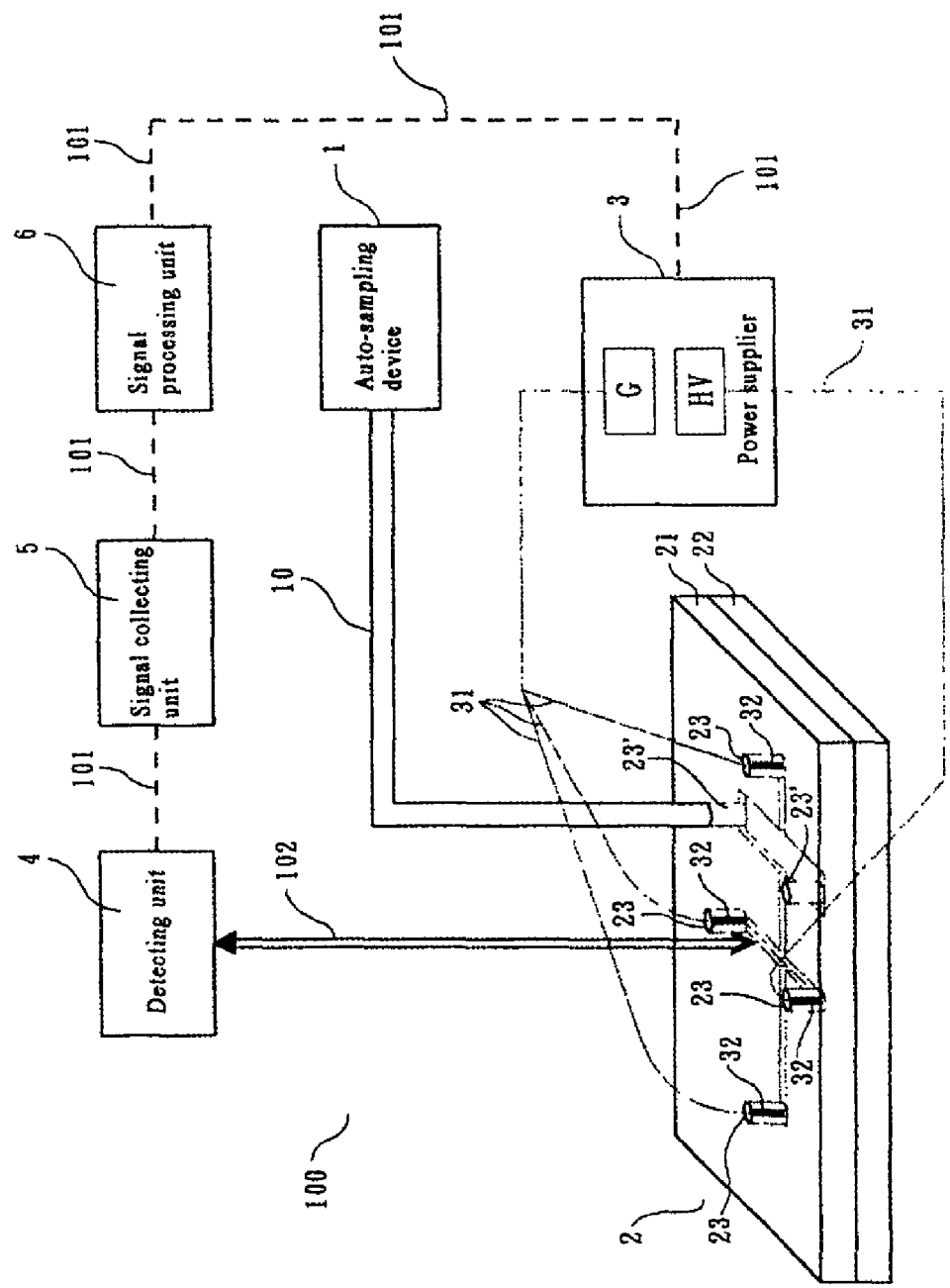
FIG. 1 illustrates for the instruments of the sample analysis system with chip-based electrophoresis device of this invention.

FIG. 1 illustrates the instruments of the sample analysis system with chip-based electrophoresis device 100 of this present invention comprising an auto-sampling device 1, which is a flow-based auto-sampling device driven by dynamic force, a chip 2, an power supplier 3, a detecting unit 4, a signal collecting unit 5, and a signal processing unit 6. During the operation, sample that needs analysis is passed through the auto-sampling device 1 via one of the port 23' on the cover plate 21 of chip 2 coupled to the connecting pipe 10 and introduced inside said chip 2. The electrode line 31 of the power supplier 3 is coupled to the electrode 32 being disposed inside the port 23 to control the sample loading detecting position by the electric voltage control, and to detect the signal of the sample by the detecting unit 49 (optical detecting unit), in which Number 102 represents the light path. The signal is transmitted through the signal line 101 to the signal collecting unit 5, and using the signal collecting unit 5 to convert the signal of the sample of the detecting unit 4 from analog signal to digital signal. Such signal is outputted from the signal line 101 to the signal processing unit 6, and then is outputted as the data for the sample analysis through the signal processing unit 6 for the sample analysis. Such analysis data is provided for research unit and medical unit to proceed with the related research work. Said power supplier 3 controls the output of the electric voltage by the signal processing unit 6 via the signal line 101 or operates manually to control the output voltage.

Figure 2:
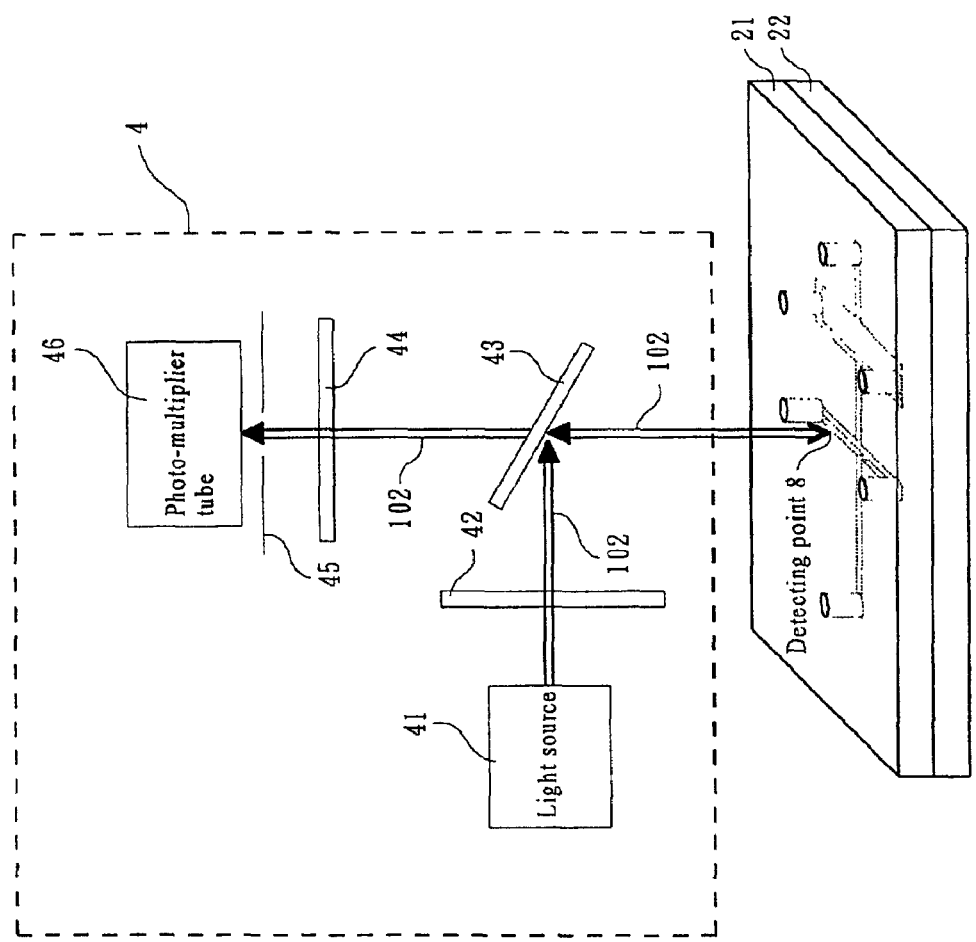
FIG. 2 illustrates the detecting unit of this invention.

Please refer to FIG. 2. The detecting unit of this invention is an optical detecting unit, and its preferred embodiment is a fluorescent detecting unit, comprising a light source 41 (such as mercury lamp, Olympus, 100 W), a lens (such as a convex lens which is not shown in the figure), an excitation filter 42, a dichoric mirror 43, an emission filter 44, a pinhole 45 (600 $\mu$m), and a photo-multiplier tube (PMT) 46. The following is its detection method: Light source 41 passes through the excitation filter 42 and selects a specific excitation wavelength (Number 102 in FIG. 2 indicates the light path) for reflection from the dichoric mirror 43 through the lens (a convex lens, which is not shown in the figure) and focuses on the detecting point 8 on the separation channel 25 of chip 2. After the light source 41 illuminates the sample at the position of the detecting point 8 on the separation channel 25, it will produce fluorescent radiation which will be collected by the lens and pass through the dichoric mirror 43, the emission filter 44, and a pinhole (600 $\mu$m) 45 to the photo-multiplier tube 46 to multiply the signal of the sample. The analog signal is converted from analog signal to digital signal by the signal collecting unit 5, and then output the data of the sample analysis via the signal processing unit 6 for further use in the experiment.

Figure 3A:
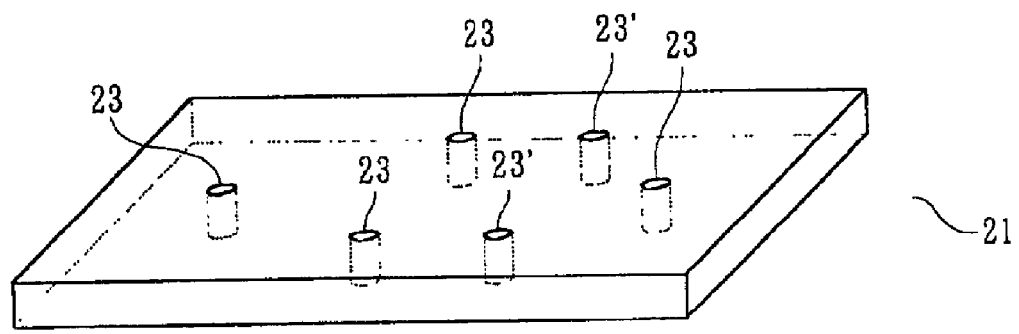
FIGS. 3A and 3B illustrate the perspective view of the cover plate and the base plate of the chip respectively of this invention.
Figure 3B:
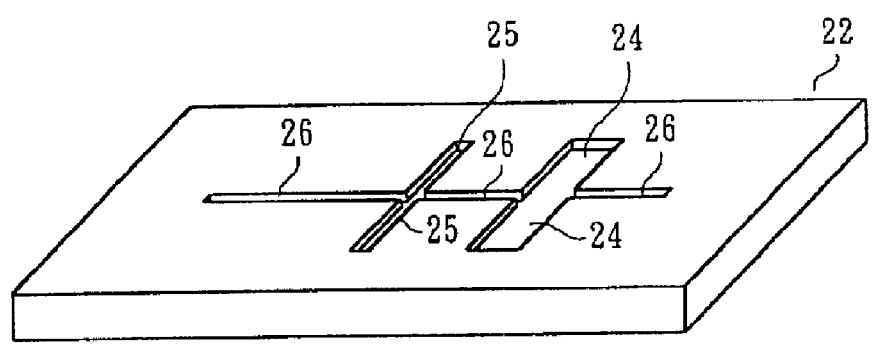

Please refer to FIGS. 3A and 3B. They show the structure of chip 2 of the sample analysis system with a chip-based electrophoresis device 100 of this invention, wherein FIG. 3A shows the cover plate 21 of chip 2; FIG. 3B shows the base plate 22 of chip 2. The cover plate 21 has a plurality of ports 23, 23' (with a diameter of 1.5 mm as an example) penetrating the cover plate 21. The base plate 22 of chip 2 comprises at least one sample loading channel 24, at least one separation channel 25, and at least one connection channel 26. The ports 23, 23' being disposed at the cover plate 21 of chip 2 respond to both ends of the sample loading channel 24, the separation channel 25, and the connection channel 26 at the base plate 22 of chip 2. The connection channel 26 connects to the channel of the sample loading channel 24 and the separation channel 25. The said port 23 is a reservoir for storing the liquid of the separation channel 25 and the connection channel 26 and placing the electrode 32, and working with the power supplier 3, electrode line 31, electrode 32, and the liquid in the reservoir to form a current path in order to attain the function of the electrophoresis. When one of the two ports 23 acts as the port for loading samples, and the other port 23' will act as the waste liquid discharge port. The excessive useless sample waste liquid is discharged through the waste liquid port into the waste liquid storage tank (not shown in the figure). Chip 2 of the present invention uses hydrofluoric acid or other equivalent technology to bind the cover plate 21 and the base plate 22 of chip 2 to produce a complete chip 2.

Figure 13:
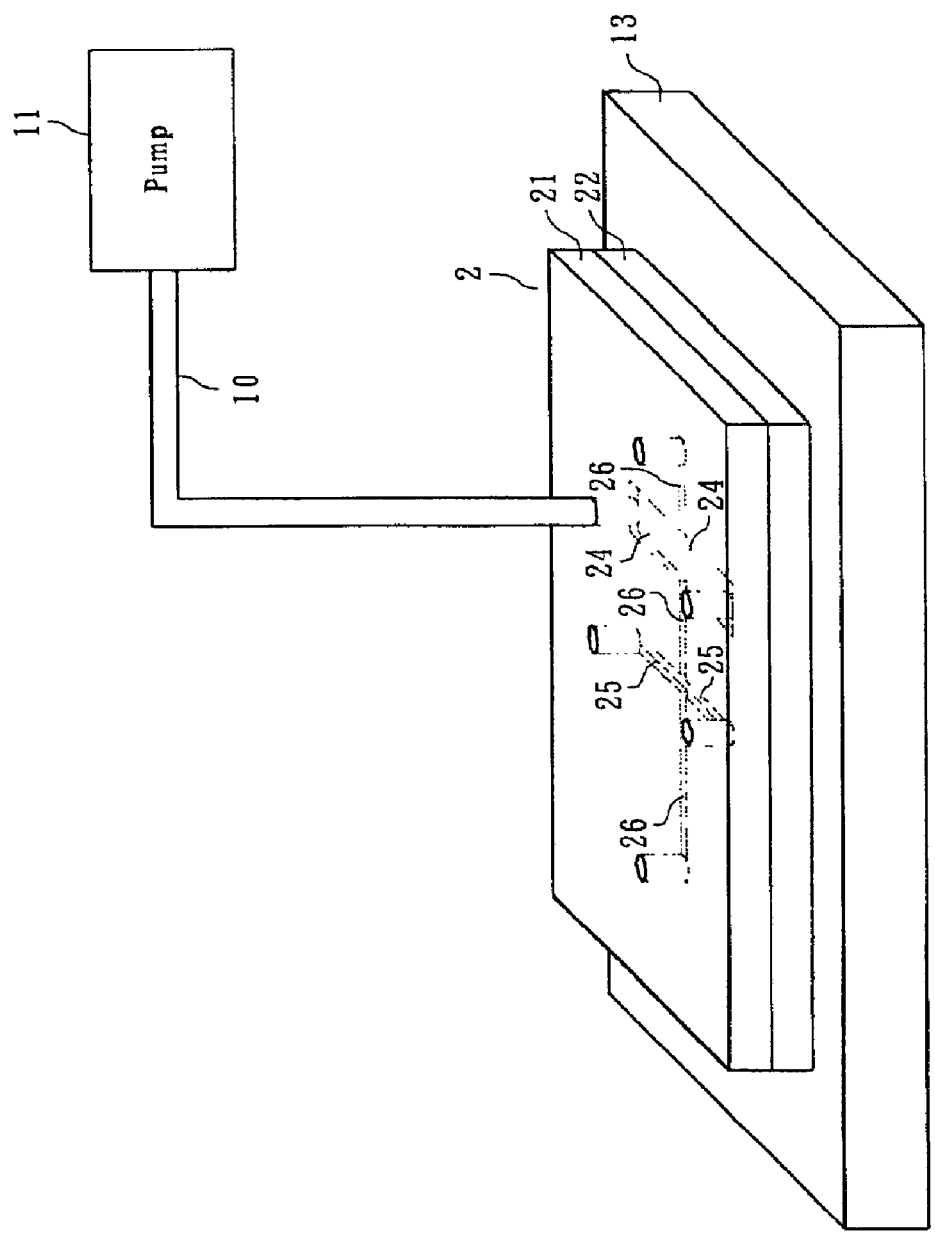
FIG. 13 illustrates the chip of this invention being coupled to the derivatization device.

Chip 2 of this invention can perform a surface modification on the sample loading channel 24 on chip 2 to prevent the sample being adhered onto the wall of the sample loading channel 24, and further to increase the sample loading rate and reduce the cross contamination of samples. The steps of the said derivatized method are listed below: Please refer to FIG. 13. After chip 2 of this invention is rinsed by evaporated water, and the sodium hydroxide of an equivalent weight concentration (1N) is introduced continuously into the sample loading channel 24 of chip 2 via the connecting pipe 10 by using the pump 11 (such as the syringe pump) for a continuous flow of several hours (preferably for 3 hours) in order to rinse the sample loading channel 24 in the base plate of chip 2. Rinse the sample loading channel 24 with evaporated water for about 30 minutes, and then use the syringe to inject acetone into the sample loading channel 24 for a rinse. Chip 2 is placed on the heating platform 13 at the temperature of about 60° C.~80° C. (preferably 80° C.) and baked to dry. Then use the syringe to inject toluene into the sample loading channel 24 for a rinse, and use a pump 11 (such as a syringe pump) to introduce 10% dimethyldichlorosilane (DMCS) or a trimethyldichlorosilane (TMCS) dissolved in toluene into the sample loading channel 24 with a constant rate via the connecting pipe 10 (wherein the TMCS gives a better effect. Use the heating platform 13 at 80° C. to proceed with the derivatization reaction (the reaction time is 1 hour). Then inject the toluene into the sample loading channel 24 by a syringe to rinse and remove the 10% DMCS or TMCS dissolved in toluene that remains after the reaction, and load the methanol into all of the channels (including sample loading channel 24, separation channel 25, and connection channel 26) that are disposed on the base plate 22 of chip 2. Let it sit still for a while (preferably about 5 minutes), and then rinse all of the channels on the base plate 22 by methanol, toluene, and acetone separately. Finally, use the heating platform 13 at 60° C.~80° C. (preferably 80° C.) to bake and dry chip 2 until the derivatization step completes.

The sample loading effect of chip 2 after the derivatization step can be proved by the following embodiment.

The First Embodiment

Figure 14:
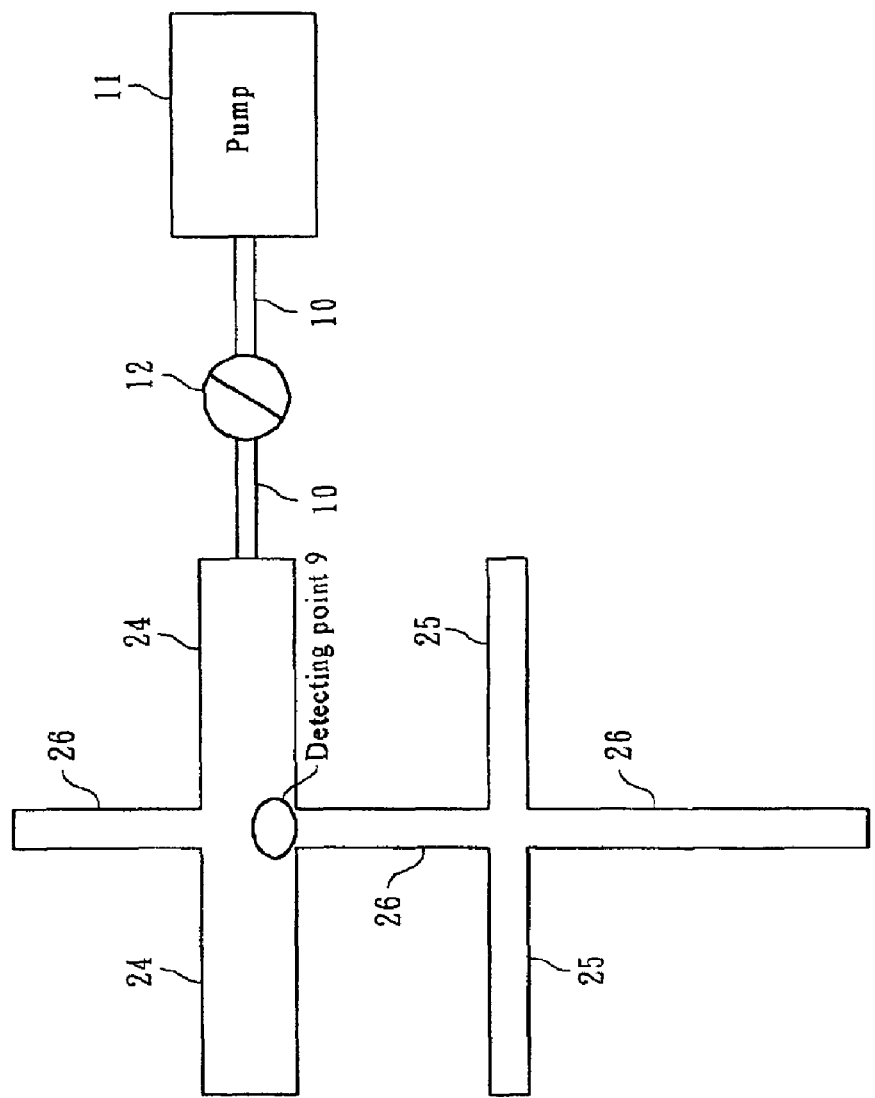
FIG. 14 illustrates the chip sample loading of this invention after detecting the derivatization.
Figure 15:
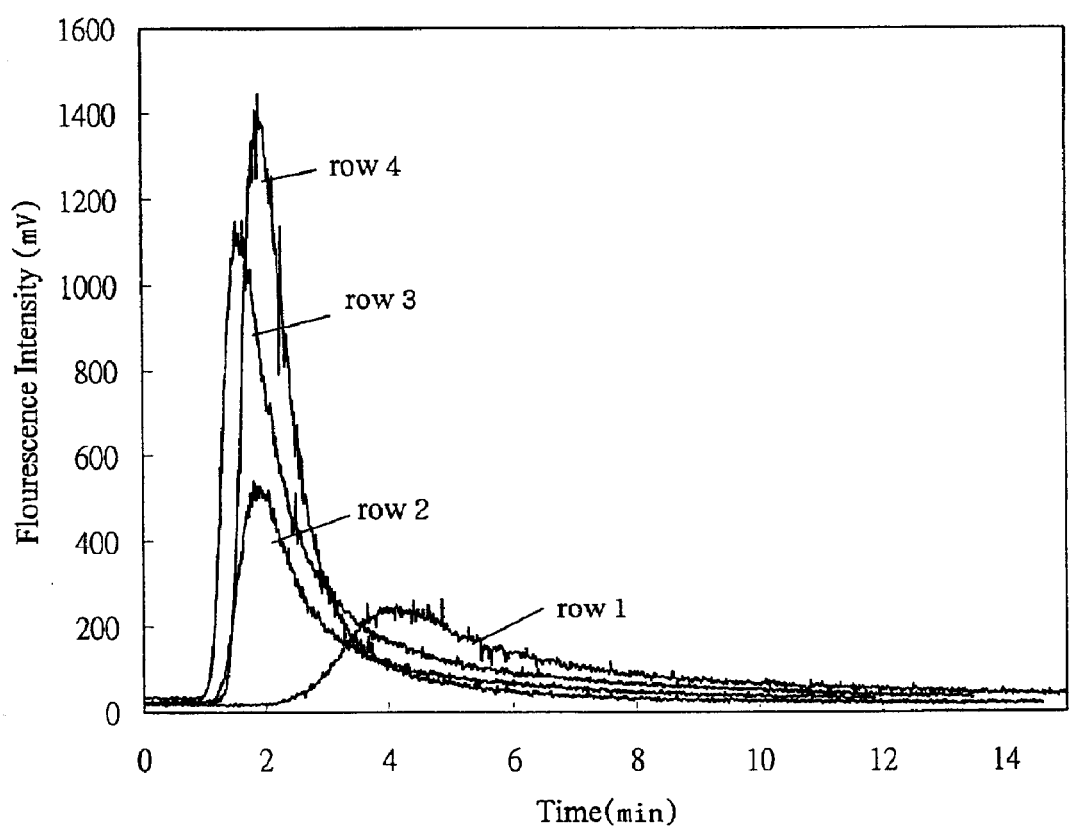
FIG. 15 illustrates the test diagram of the chip sample loading under different derivatization conditions of this invention.

The first embodiment compares the chip undergoes the derivatization reaction under four different conditions including: the sample loading effects of non-derivatization chip (row 1), chip that is derivatization in 10% DMCS dissolved in toluene for an hour at room temperature (row 2), chip that is derivatization in 10% TMCS dissolved in toluene for an hour at room temperature (row 3), and chip that is derivatization in 10% TMCS dissolved in toluene for an hour under 80° C. (row 4). Other experimental conditions are: The concentration of the sample (Rhodamine B) is $2 \times 10^{-4}$M, the volume of the injected sample is 60 nL, and the flow rate of the pump 11 is 5.0 $\mu$L/min. In FIG. 14, this embodiment is detected without adding any electric voltage. After the sample is loaded into injector 12, it is introduced into the sample loading channel 24 by pump 11, and then performs the detection at the position of detecting point 9. The detected result of this embodiment is shown in FIG. 15. The spectrum at row 1 (non-derivatization chip) with respect to the sample loading rate shows that the time required for the sample to reach the detecting point 9 is longer than those from row 2 to row 4. With respect to the detection intensity, the chip of different derivatization condition will also generate different results. The results of row 1 to row 4 show that the chip that is derivatization in 10% TMCS dissolved in toluene for an hour under 80° C. (row 4) has the best sample loading effect, and FIG. 15 also shows the reduction of sample being adhered on the sample loading channel 24 after derivatization method and hence it increase the sample loading rate as well as the strength of sample detection.

The said derivatization step of the present invention is widely used as the material for the Si—OH surface material (such as the channel of the chip and capillary) to prevent the sample being adhered to the material surface (such as the channel wall and pipe wall) causing the pollution that will affect the result of sample analysis, and increase the sample loading rate.

Figure 4:
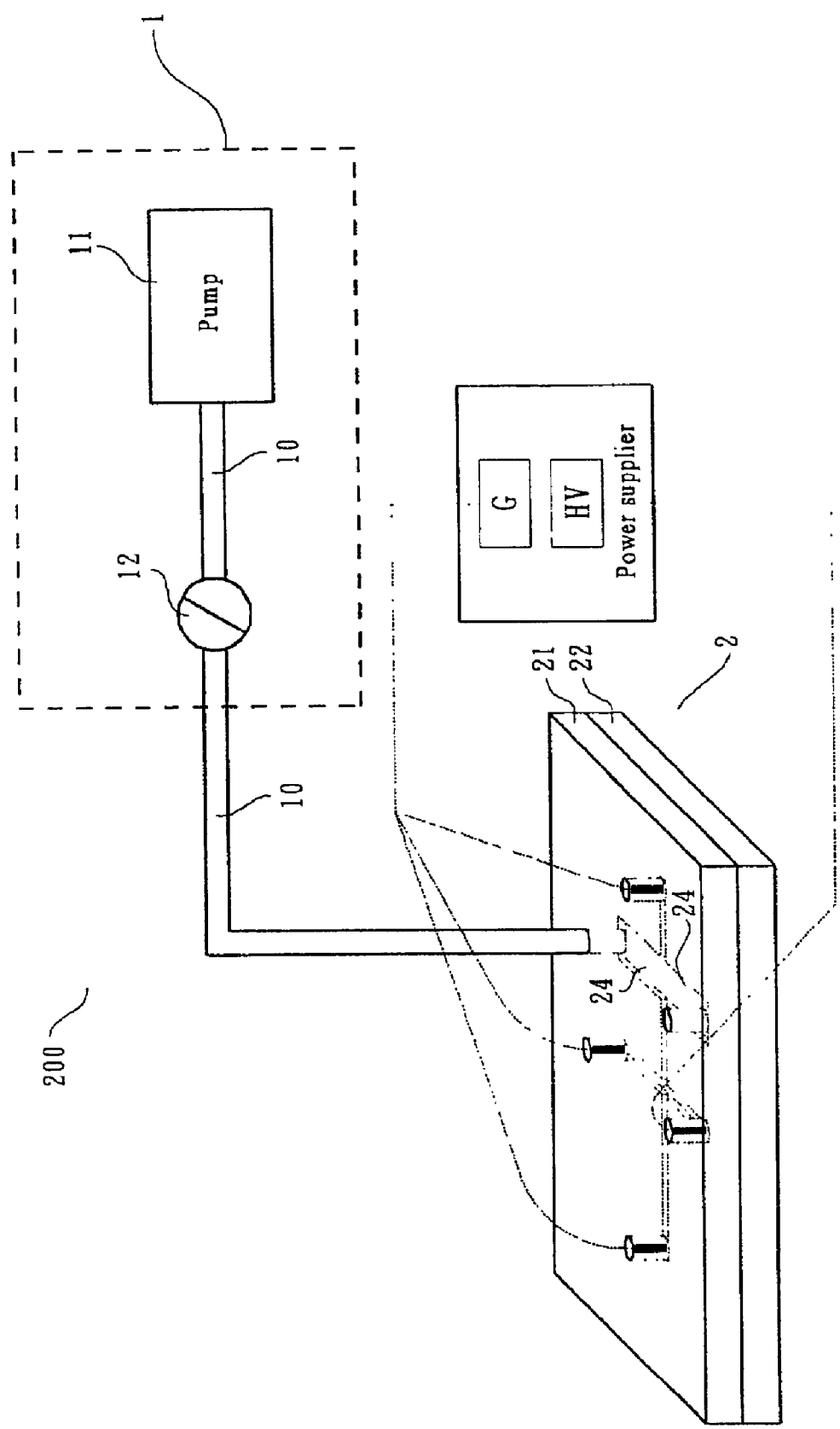
FIG. 4 illustrates the chip-based electrophoresis device of this invention being connected to the auto-sampling device (in discrete mode of sample introduction).

The auto-sampling device 1 driven by dynamic force according to the present invention comprises two sample loading models: the continuous mode and the discrete mode of sample introduction. The continuous mode such as the microdialysis performs the in-vivo sampling on animal samples, and introduces the continuously obtained sample into chip 2 for analysis by the said auto-sampling device 1. The discrete mode of sample introduction as shown in FIG. 4 illustrates the chip 2 connects to the auto-sampling device 1 (discrete mode of sample introduction, comprising a pump 11 and an injector 12, and the injector 12 has sample loading grooves for a constant volume of sample (not shown in the Figure) can adjust the volume (such as 60 nL or 100 nL) according to the actual needs. The sample loading procedure is to set injector 12 to the loading mode and then load the sample into said sample loading groove of the injector 12, and then set the loaded injector to the injection mode. Use the pump 11 to send out the sample into injector 12 by constant flow rate via the connecting pipe 10', and introduce the sample into the sample loading channel 24 through the port 23' of the connecting channel 10, and the sample can be introduced continuously into said chip 2 for analysis through the connected auto-sampling device 1.

Figure 5B:
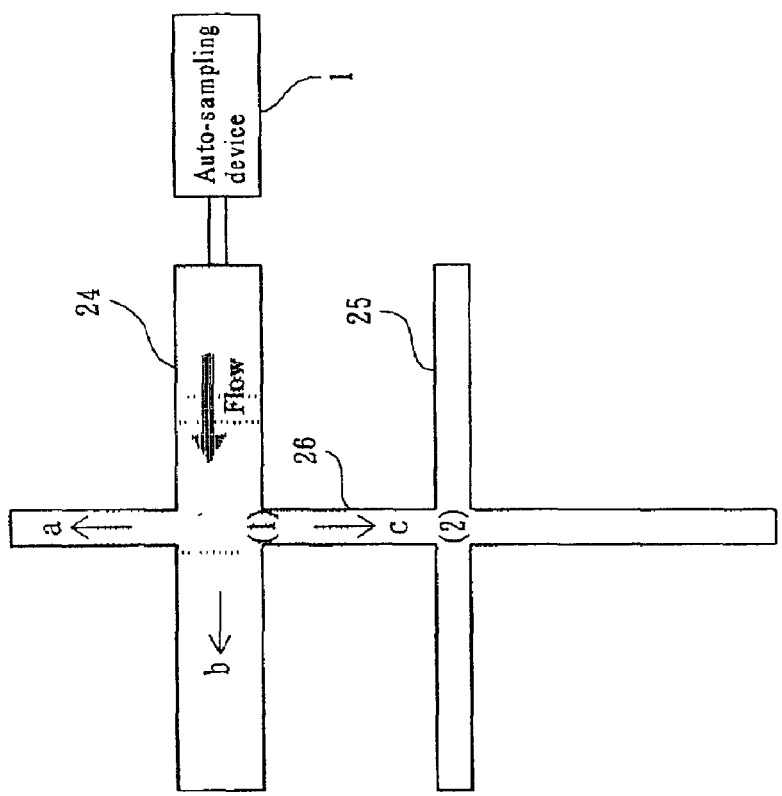
FIGS. 5A, 5B, and 5C illustrate the sample loading procedure of the chip-based electrophoresis device respectively of this invention.
Figure 5A:
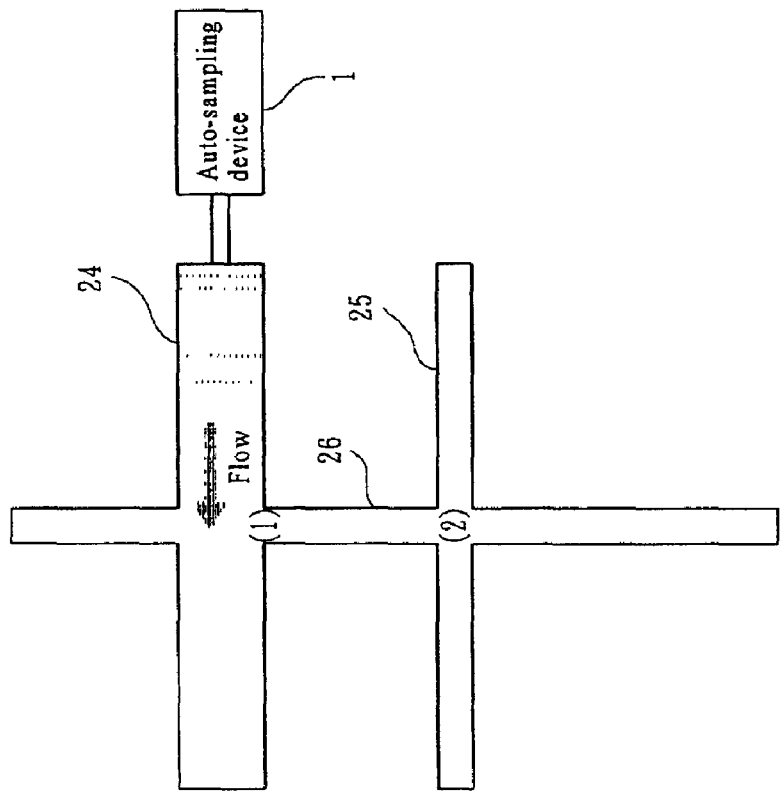
Figure 5C:
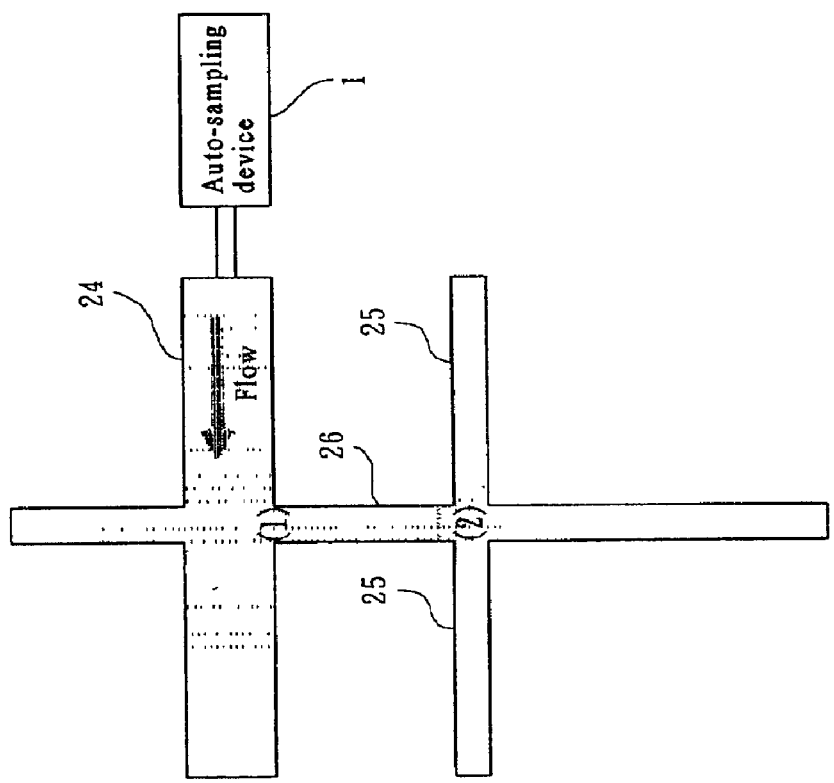

From any of the modes, the sample is introduced into chip 2 as shown in FIG. 5A, and the sample is introduced into the sample channel 26 of chip 2 by the auto-sampling device 1. As the pump 11 brings the liquid flow to carry the sample into the intersection (1) of the sample loading channel 24 and the connection channel 26. As shown in FIG. 5B, when the sample flows to the intersection (1), the sample will split into the flows into three directions of the channels at the intersections a, b, and c according to the diameter of the channels of the sampling loading channel 24 and the connection channel 26. After a period of time, the sample flows along the direction c of the sample loading channel 24 to the intersection (2) of the separation channel 25 and the connection channel 26 as shown in FIG. 5C.

Figure 6A:
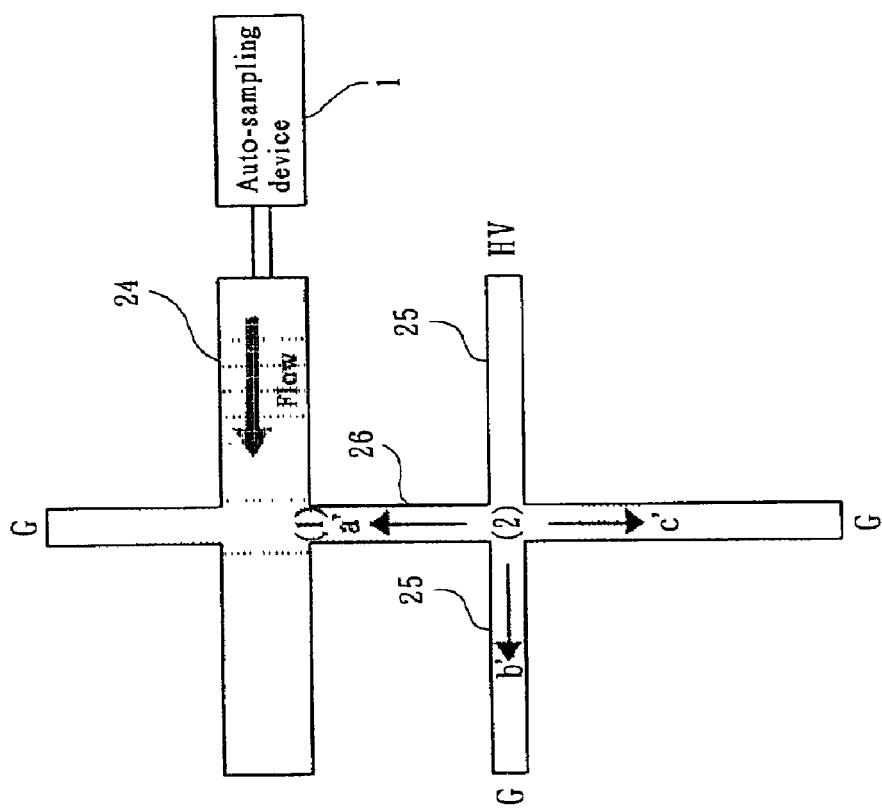
FIGS. 6A and 6B illustrate the sample flow of the chip-based electrophoresis device after the sample loading procedure and the electric voltage control process as in the processes shown in FIGS. 5A, 5B, and 5C.
Figure 6B:
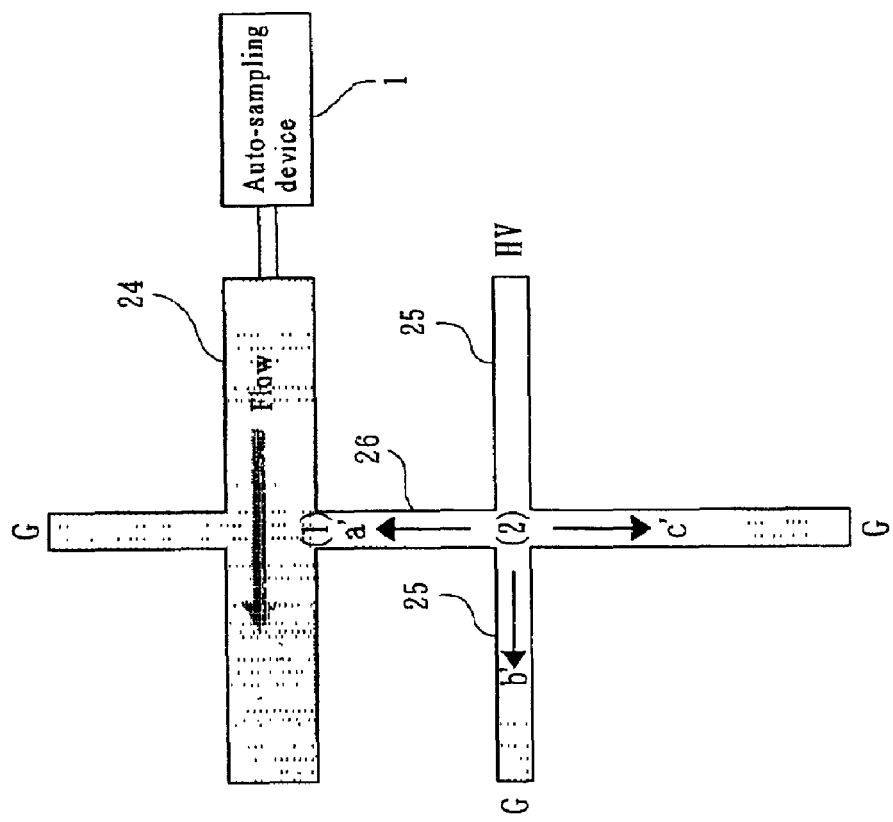

In FIG. 6A, the symbol G stands for ground, and HV for high voltage, and both G and HV represent the ground and high voltage of the power supplier 3. When the sample flows to the intersection (2), the power supplier 3 applies a certain electric voltage to the sample, and the sample entering the intersection (2) shifts from HV to G under the affection of electric field, and moves in the three directions a', b', and c' as shown in FIG. 5A, wherein the sample that moves in the direction b' is introduced into the separation channel 25 for separation, and the sample that has not reached the intersection (2) is brought back to the sample loading channel 24 due to the electric field effect. In FIG. 6B, the continuous flow stream in the sample loading channel 24 brings the unwanted sample to waste liquid tank (not shown in the figure) in order to prevent the sample that has previously entered into the separation channel 25 for the separation from being interfered by the sample that enters into the sample loading channel 24 later. Since the electric field effect (that is generated from the critical pinching voltage as described below) can accurately control the flow direction of the sample, the sample at another time period will not split into other channels to interfere the sample analysis.

Figure 7:
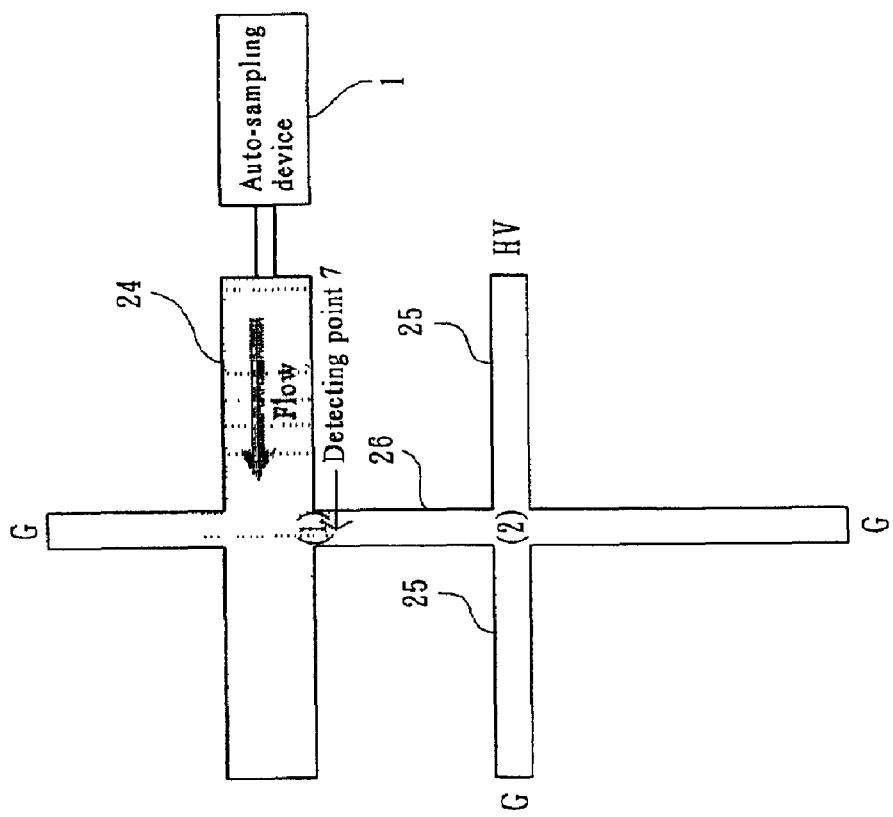
FIG. 7 illustrates the relationship between the flow rate and the critical pinching voltage with a chip-based electrophoresis device of this invention.

The present invention further studies the relation of the flow rate of the pump 11 and the critical pinching voltage (the critical pinching voltage means the electric voltage required for the liquid split flow rate reaches an equilibrium) in order to optimize the analysis effect by controlling the voltage of the power supplier 3 during the sample analysis performed at a later time. In FIG. 7, the sample is introduced into the sample loading channel 24 of chip 2 through the auto-sampling device 2. When the sample reaches the detecting point 7 of the connection channel 26 as shown in FIG. 7, the detecting unit 4 will detect the signal of the sample, and the power supplier 3 will apply an electric voltage on the sample generating an electroosmosis flow force that will conflict with the flow split force generated by the pressure induction. If the electroosmosis flow force is greater than the split flow force of the induced pressure, then the sample will be pushed back to the sample loading channel 24, and the flowing liquid in the sample loading channel 24 brings the sample back to the other end of the sample loading channel 24 and introduce the sample into the waste liquid channel for collection (not shown in the figure). On the contrary, if the split flow force of the induced pressure is larger than the electroosmosis flow force, then the sample will continue to move and disperse along the direction from the connection channel 26 to the intersection (2) and causes an interference to the sample that has entered into the separation channel 25 at a later time for sample analysis. The position of the detecting point 7 as shown in FIG. 7 is another detecting point for performing the experiment on the relation of the liquid flow rate of the pump 11 and the critical pinching voltage. However, when the actual experiment is performed, the position of the detecting point should be set on the separation channel 25 and between the intersection (2) and the position of G for detection.

According to the study of the experiment, the relation between the liquid flow rate of the pump 11 and the critical pinching voltage is shown in FIG. 8, and the data shown in FIG. 8 can be used to set up the related operating conditions in the embodiment.

In the sample analysis system with chip-based electrophoresis device 100 according to the present invention, the reproducibility of the sampling under continuous mode of the auto-sampling device 1 will be tested in the following embodiment:

The Second Embodiment

Figure 11:
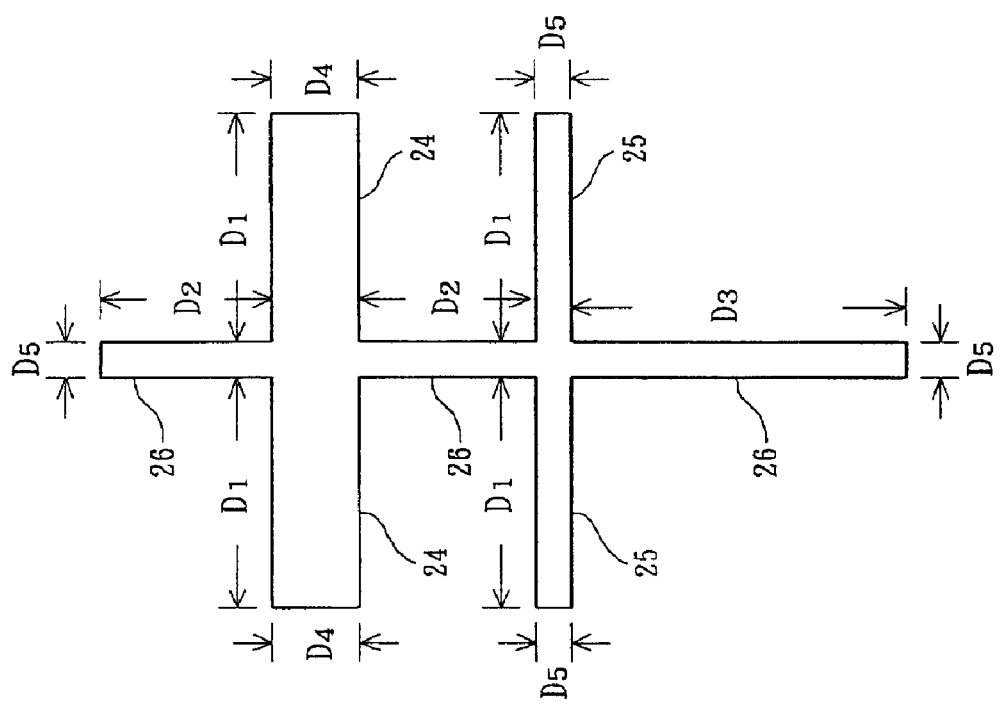
FIG. 11 illustrates the geometric structural diagram of this invention showing the channel at the base plate of the chip.

The second embodiment incorporates Rhodamine B as the sample for the sample analysis system with chip-based electrophoresis device 100 of this invention, and the settings for the experiment conditions are described below: the geometric structure of the channels on the base plate 22 of chip 2 are shown in FIG. 11, $D_1$ is 2 cm, $D_2$ is 1.5 cm, $D_3$ is 4 cm, $D_4$ is 3 mm, and $D_5$ is 120 $\mu$m; the depths of the sample loading channel 24, separation channel 25, and connection channel 26 are all 40 $\mu$m; the flow rate of the pump is 5 $\mu$L/min.; the electric voltage is 3.3 kv; the voltage applying time is 48 seconds, and the detecting unit is a fluorescence detecting system.

Figure 9:
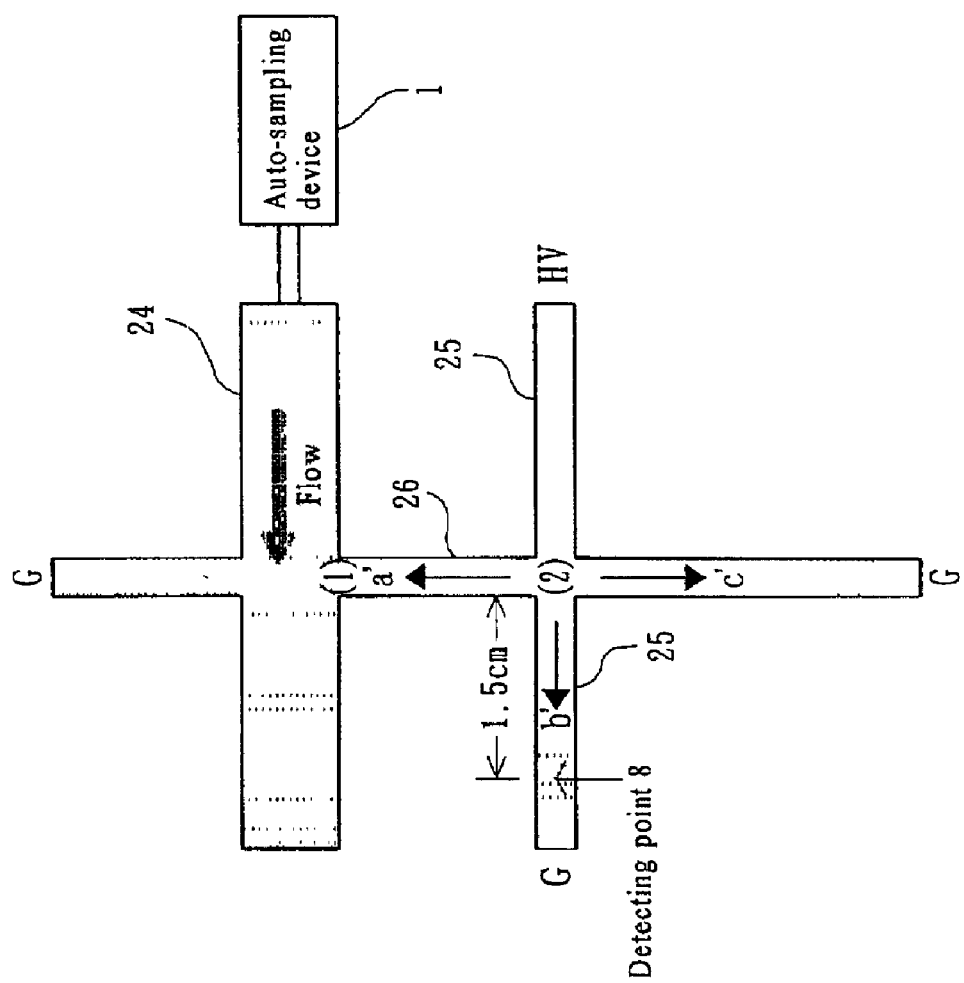
FIG. 9 illustrates the detecting point of the sample analysis system with chip-based electrophoresis device of this invention.
Figure 10:
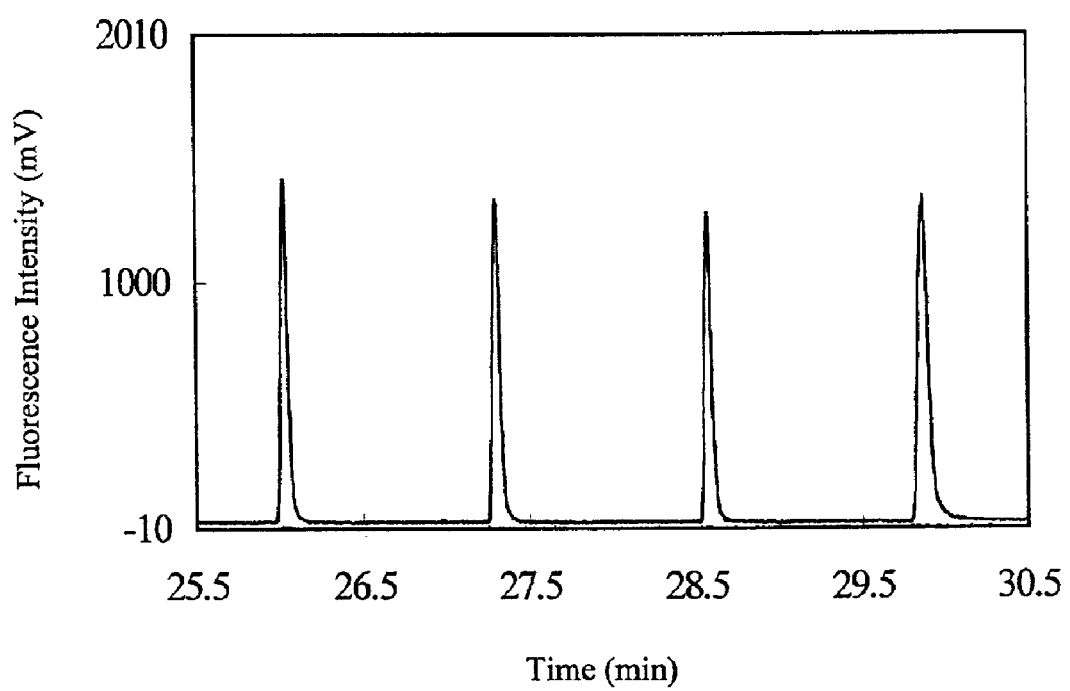
FIG. 10 illustrates the test diagram of the reproducibility of the continuous mode of sample introduction with respect to the sample analysis system with chip-based electrophoresis device of this invention.

In FIG. 9, the sample is introduced into the sample loading channel 24 after the continuous sampling process, the sample will follow the flow stream as illustrated in FIGS. 5 and 6 to the detecting point 8 of the separation channel 25 as shown in FIG. 9, and the distance between the detecting point 8 and the connection channel 26 is 1.5 (as shown in FIG. 9). By the continuous sample signal detected by the detecting unit 4 and the conversion of the detected signal from analog into digital, the signal will be outputted via the signal processing unit 6. The result of the above embodiment is shown in FIG. 10. The spectrum shown in FIG. 10 outputs the result by the signal processing unit 6 indicating that the sample analysis system with a chip-based electrophoresis device 100 of this invention has excellent effect on the reproducibility with respect to the result continuous mode of sample introduction.

Furthermore, the sample analysis system with chip electrophoresis device 100 of this invention can be applied to analyze the same sample with different concentrations under the discrete mode of sample introduction of the auto-sampling device 1, and will be further described in the following embodiment.

The Third Embodiment

The third embodiment describes the application of the sample analysis system with chip electrophoresis device 100 of this invention as shown in FIG. 1, and the continuous detection concentrations are respectively $10^{-5}$M, $4 \times 10^{-5}$M and $10^{-4}$M of the same sample (Rhodamine B), and the setting for the experiment conditions are as follows: the geometric structure of the channels on the base plate 22 of chip 2 are shown in FIG. 11; $D_1$ is 2 cm, $D_2$ is 1.5 cm, $D_3$ is 4cm, $D_4$ is 3 mm, and $D_5$ is 120 $\mu$m; the depths of the sample loading channel 24, separation channel 25, and connection channel 26 are all 40 $\mu$m; the flow rate of the pump is 5 $\mu$L/min.; the electric voltage is 1.2 kv; the voltage applying time is 6.5 minutes, the injected volume of sample is 60 nL, and the detecting unit is a fluorescence detecting system.

Figure 12:
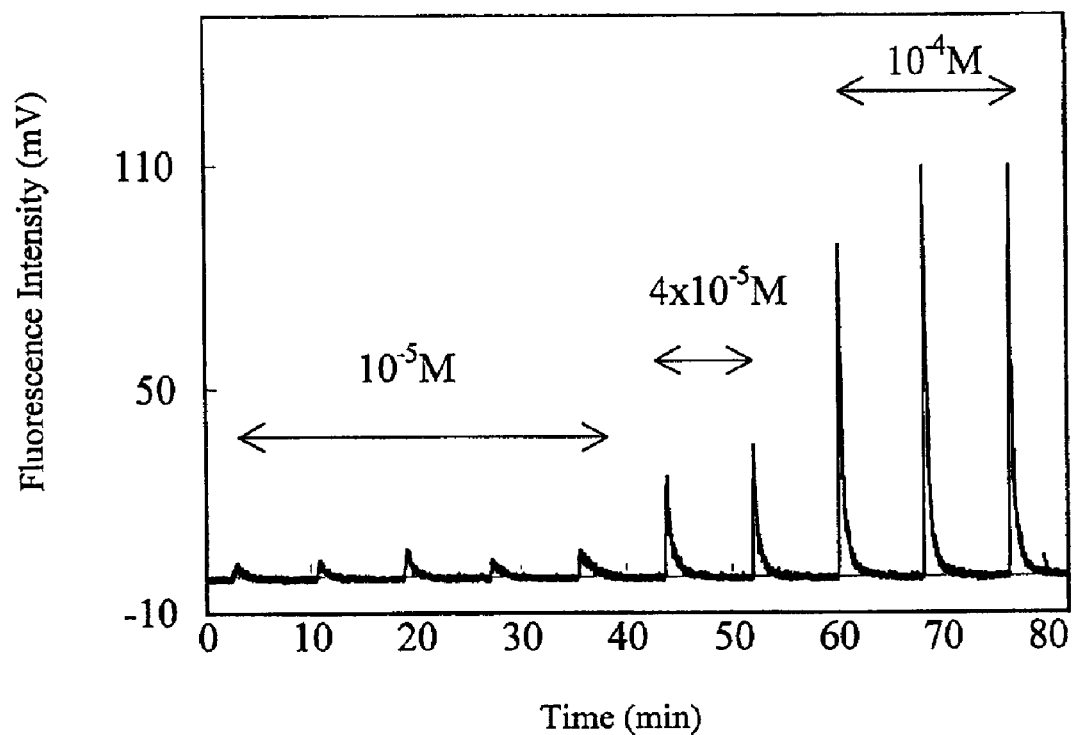
FIG. 12 illustrates the test diagram of the discrete mode of sample introduction of the same sample with different concentrations with respect to the sample analysis system with chip-based electrophoresis device of this invention.

The result of the experiment being performed according to the above conditions is shown in FIG. 12 wherein after five times of the continuous mode of sample introduction of the $10^{-5}$M sample, and two times of the continuous mode of the $4\times10^{-5}$M sample, and finally three times of the continuous mode of the $10^{-4}$M sample. The continuous detection result shown in FIG. 11 indicates that the sample analysis system with chip-based electrophoresis device 100 of this invention can perform the discrete mode of the same sample with different concentrations and possess the excellent reproducibility and high sensitivity properties, and not being interfered by the sample that enters into the system at other time. The system of the present invention can be further applied for the analysis of sample with different concentration of different samples, or different samples of the same concentration.

Another embodiment of the present invention may change the way of the voltage being applied to the chip, and it may reduce the sample from being interfered by the electric field, gains better effect on the analysis result and provides a wider application. The advantages and implementation will be described in details with the diagrams in the following embodiment.

Figure 16B:
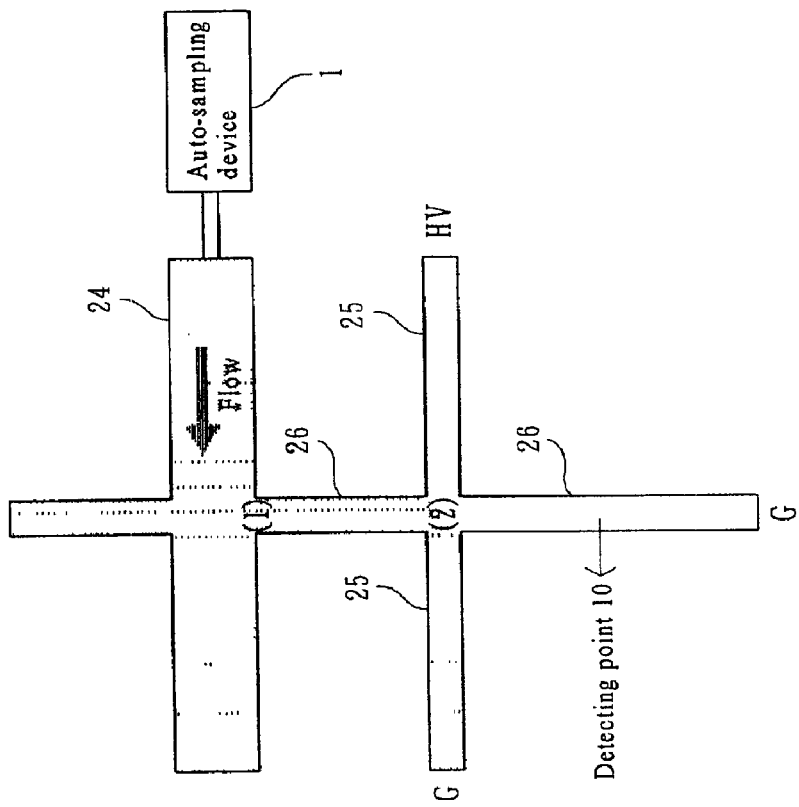
FIGS. 16A, 16B, 16C, and 16D illustrate the sample loading procedure of this invention using another electric voltage mode to introduce the sample into the detecting point.
Figure 16A:
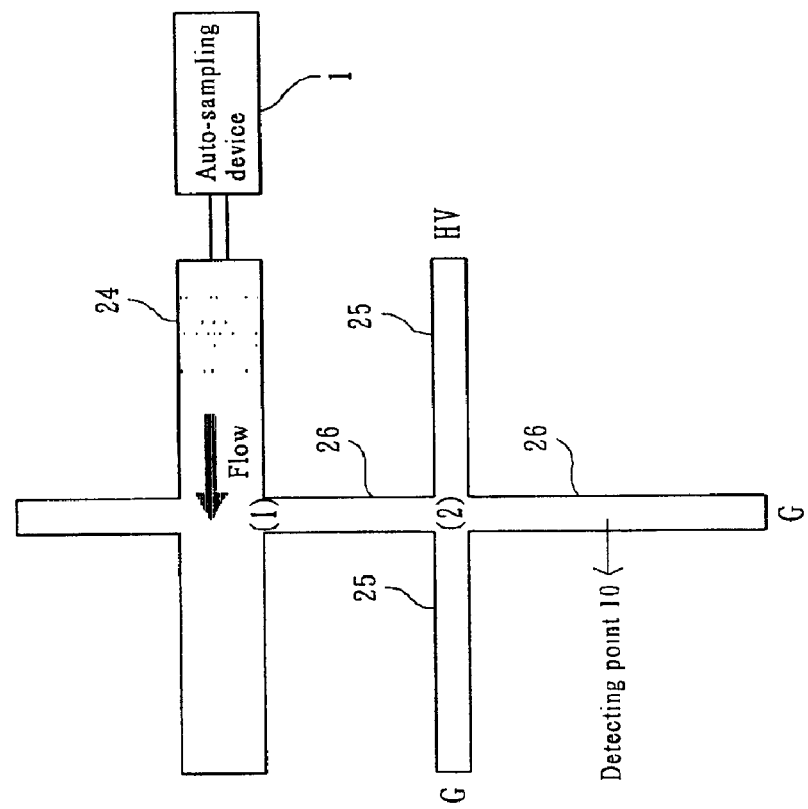
Figure 16D:
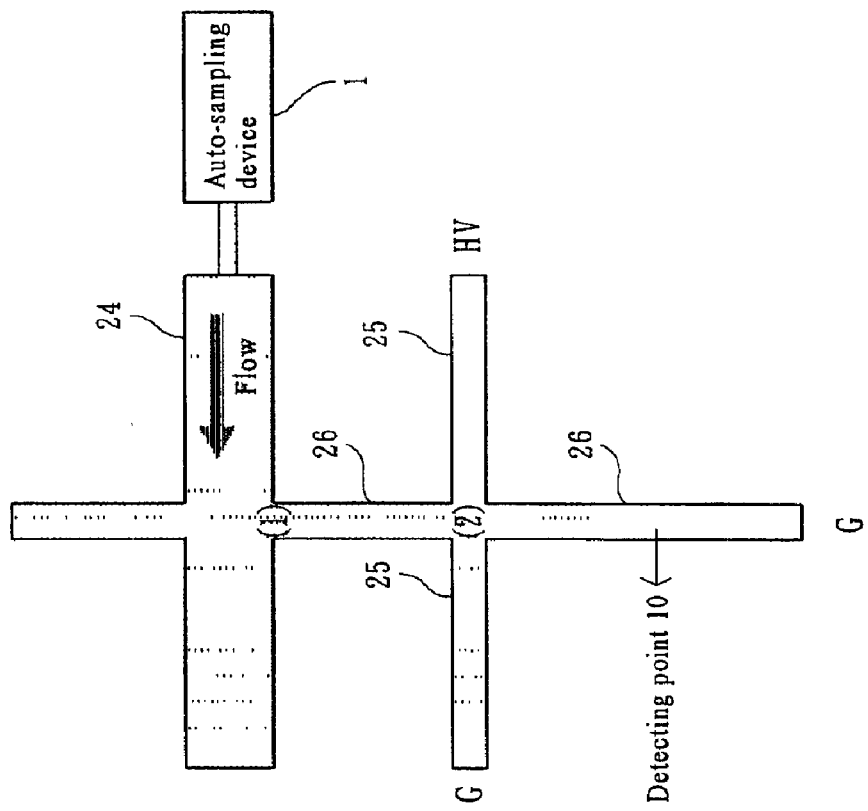
Figure 16C:
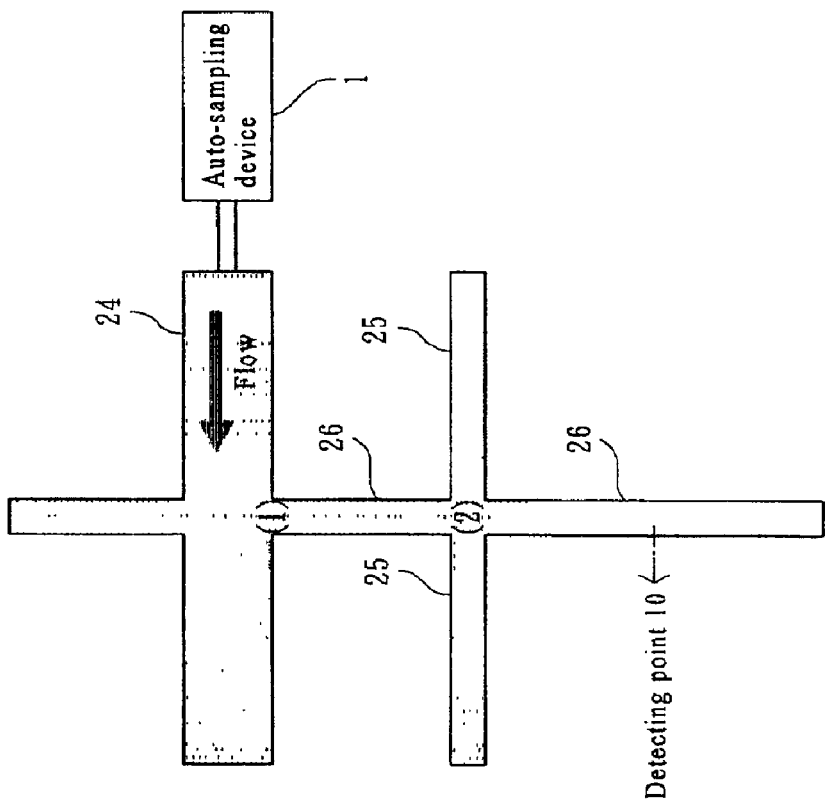

In FIGS. 16A to 16D, when the auto-sampling device 1 introduces the sample into the chip (the chip structure is shown in FIG. 11) by fluid driving mode, meanwhile the power supplier continues to apply electric voltage on the chip. The high voltage (HV) and ground (G) are layout as shown FIG. 16A. In the introduction process of the sample into the chip, first, an electrical voltage was applied to the chip. The sample flow passed the intersection (1) and then moved to ground G through the intersection (2) (as shown in FIGS. 16A and 16B). For sample loading and separation, the chip-based electrophoresis device was turned to the floating mode for a present period of time that determined the amount of samples "loaded" into the separation channel 26 (as shown in FIG. 16C). Then, an electrical voltage was immediately applied to the chip to start the sample separation (as shown in FIG. 16D). By applying the above electric voltage, it can increase the sample loading rate and reduce the time for the sample analysis. To comply with the foregoing sample introduction mode, the chip of the present invention from the intersection (2) to the ground terminal G of the connecting channel 26 is for separating the sample. Actually, the channels at the base plate of the chip (that is the sample loading channel 24, the separation channel 25, and the connection channel 26) can be altered according to the actual situation of the application (for example, the usage of the separation channel 25 and that of the connection channel 26 are interchangeable, and they are not restricted by the names used in this specification).

The other feature of applying the electric voltage as shown in FIG. 16, starting from sampling at the sample loading channel 24 and all through the analysis procedure, the system is kept free of electric fields. Since all kinds of bio-reactions are affected by the electric field interference very easily, therefore performing experiment free of electric fields can give the best result. Such electric field free status allows the surface treatments on the chip of the present invention such as the immobilization of matter including antigen, antibody, protein, or enzyme, and performs specific bio-reaction, apply such in different kinds of biotech analysis (including the spectrum analysis, protein quick selection and comparison, drug analysis, etc.).

The Fourth Embodiment

Figure 17:
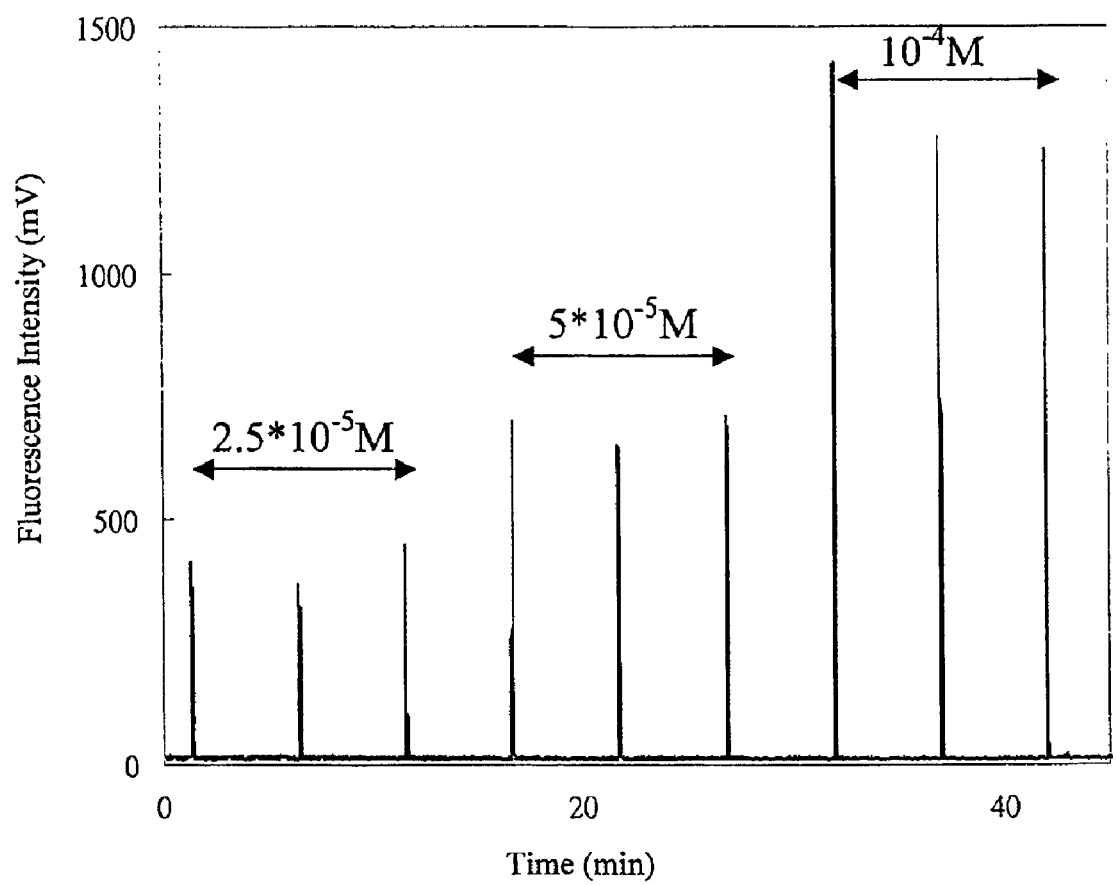
FIG. 17 illustrates the test diagram of the discrete mode of sample introduction of the same sample with different concentrations with respect to the sample analysis system with chip-based electrophoresis device of this invention (which incorporates the sample loading as shown in FIG. 16).

The fourth embodiment: By using the sample analysis system with chip-based electrophoresis device 100, and working with the continuous introduction of sample into the chip by applying electric voltage. Continuously detect the concentrations of $2.5\times10^{-5}$M, $5\times10^{-5}$M, and $10^{-4}$M of the same sample (Rhodamine B), and the setting for the experiment conditions are as follows: the geometric structure of chip 2 is shown in FIG. 11, the flow rate of the pump is 5 $\mu$L/min, the electric voltage is 1.3 kv, the applying time of electric voltage is 4.0 minutes, and the injected volume of sample is 60 nL. The result is shown in FIG. 17. The sample analysis system with chip-based electrophoresis device 100 of this invention can work with the discrete mode of sampling analysis to the same sample of different concentrations, and obtains an excellent reproducibility and high sensitivity effect, and will not be interfered by samples that enter the system at other time.

The Fifth Embodiment

Figure 18:
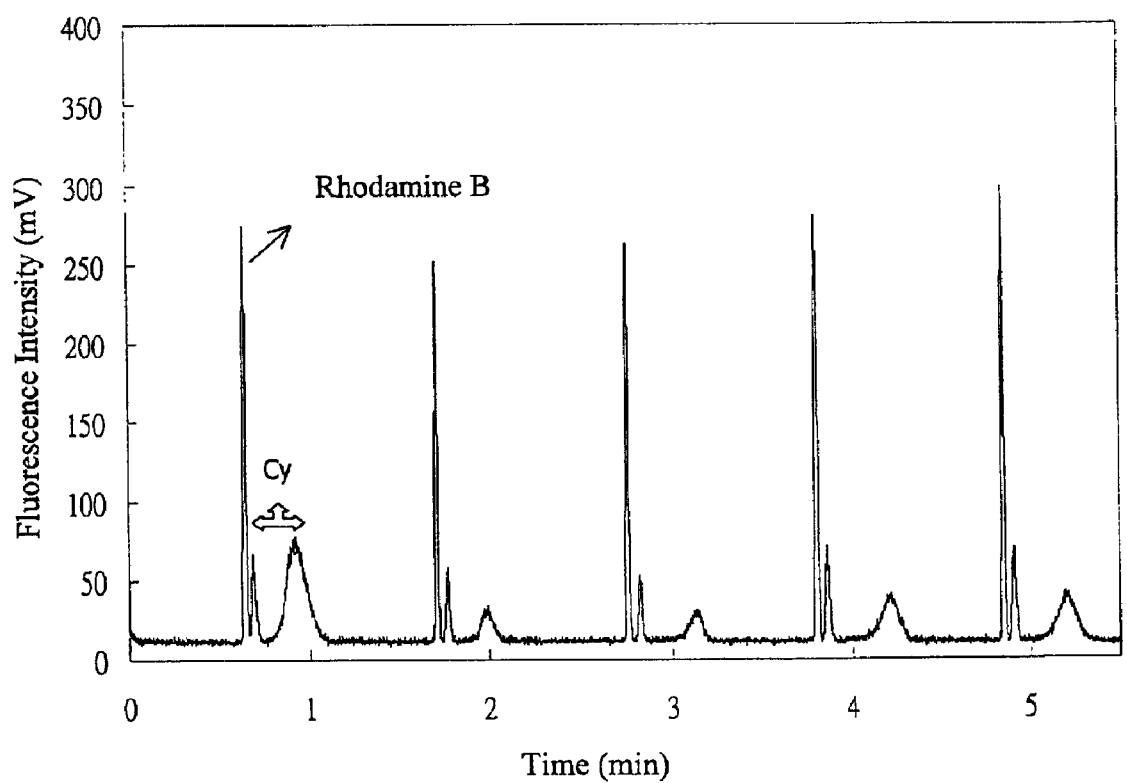
FIG. 18 illustrates the spectrum diagram of the analyzing mixture sample of the sample analysis system with chip-based electrophoresis device of this invention (which incorporates the sample loading as shown in FIG. 16).

The fifth embodiment makes use of the sample analysis system with chip-based electrophoresis device 100, and works with the continuous introduction of the sample into the chip by applying electric voltage to separate the mixture. The experiment conditions are as follows: the sample is the mixture of Rhodamine B, and $6.5\times10^{-5}$M of the Cy3 dissolved in 20 mM $Na_2CO_3$, the flow rate of the pump is 7 $\mu$L/min, the electric voltage is 1.3 kv, the applying time of electric voltage is 1.0 minute, and the result is shown in FIG. 18. This system of this invention can successfully separate the mixture of the sample and obtain a good reproducibility.

The present invention relates to a sample analysis system with chip-based electrophoresis device, more particularly, said chip electrophoresis is connected to the flow-based auto-sampling device by dynamic force to introduce the sample into the chip-based electrophoresis device for a fast and accurate analysis, which improves the shortcomings of the continuous sample analysis by traditional capillary electrophoresis, and the high sensitivity of the chip-based electrophoresis device and its analysis system is suitable for analyzing small quantity of sample. The derivatization process of the chip performs a surface modification to prevent the sample from being adhered onto the wall of the simple loading channel, and further increases the sample loading rate and reduces the cross contamination of samples. The derivatization method of this invention is not restricted to be used on chips only, and any other applications of the same purpose with the derivatization method can be performed. Therefore, this invention can be used in the analysis field such as medical detection, quick sample analysis, and in-vivo sampling of animal sample, etc. to benefit the society of human beings.

In summary of the above description, this invention enhances the performance than the conventional structure and further complies with the patent application requirements and is submitted to the Patent and Trademark Office for review and granting of the commensurate patent rights.

While the invention has been described by way of example and in terms of a preferred embodiment, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A sample analysis system with chip-based electrophoresis device, comprising:
   an auto-sampling device for loading and introducing a sample into a channel, wherein said auto-sampling device is a flow-based auto-sampling device driven by dynamic force, and said auto-sampling device comprises the continuous mode and the discrete mode of sample introduction;
   a chip for loading an separation of the sample, wherein said chip comprises at least one sample loading channel, at least one separation channel and at least one connection channel for connecting said sample loading channel and said separation channel;
   a power supplier for providing electric voltage to said chip and separating said sample;
   a detecting unit for detecting the signal generated by said sample;
   a signal collecting unit for collecting the signal of the sample detected by the detecting unit; and
   a signal processing unit for outputting said signal.

2. The sample analysis system with chip-based electrophoresis device as claimed in claim 1; wherein said discrete mode of sample introduction of the auto-sampling device comprises a pump and an injector.

3. The sample analysis system with chip-based electrophoresis device as claimed in claim 1; wherein said continuous mode of sample introduction of the auto-sampling device continuously loading sample by means of a microdialysis method.

4. The sample analysis system with chip-based electrophoresis device as claimed in claim 1; wherein said detecting unit is an optical detecting unit.

5. The sample analysis system with chip-based electrophoresis device as claimed in claim 4; wherein said optical detecting unit is a fluorescent detecting unit which comprises a light source, a lens, an excitation filter, a dichoric mirror, an emission filter, a pinhole, and a photo-multiplier tube.

6. The sample analysis system with chip-based electrophoresis device as claimed in claim 1; wherein said signal processing unit is a computer.

7. The sample analysis system with chip-based electrophoresis device as claimed in claim 1; wherein said signal collecting unit converts the collected signal of the sample from analog signal into digital signal.

8. The sample analysis system with chip-based electrophoresis device as claimed in claim 1; wherein said sample loading channel being applied by hydrodynamic force generates no electrical field.

9. The sample analysis system with a chip-based electrophoresis device as claimed in claim 8; wherein said sample loading channel without electric field is able to perform different treatments on its surface for specific bio-reaction of the sample, and then introduce the sample into the separation channel of the chip for immediate online analysis and detection.

10. The sample analysis system with a chip-based electrophoresis device as claimed in claim 9; wherein said surface treatment on the surface of the sample loading channel comprises the immobilized matter of antigen, antibody protein and enzyme.

* * * * *